United States Patent
Suzuki (10) Patent No.: US 7,525,116 B2
(45) Date of Patent: Apr. 28, 2009

(54) APPARATUS FOR AND METHOD OF ERASING RESIDUAL RADIATION IMAGE

(75) Inventor: Kiyotaka Suzuki, Odawara (JP)

(73) Assignee: FUJIFILM Corporation, Tokyo (JP)

(*) Notice: Subject to any disclaimer, the term of this patent is extended or adjusted under 35 U.S.C. 154(b) by 242 days.

(21) Appl. No.: 11/506,903

(22) Filed: Aug. 21, 2006

(65) Prior Publication Data

US 2007/0045576 A1 Mar. 1, 2007

(30) Foreign Application Priority Data

Aug. 24, 2005 (JP) ............................. 2005-243227

(51) Int. Cl.
*G11B 7/0055* (2006.01)

(52) U.S. Cl. ...................................... 250/588

(58) Field of Classification Search ................ 250/588
See application file for complete search history.

(56) References Cited

U.S. PATENT DOCUMENTS

| | | | | |
|---|---|---|---|---|
| 4,439,682 A * | 3/1984 | Matsumoto et al. | .......... | 250/588 |
| 4,786,808 A * | 11/1988 | Saito | .......... | 250/588 |
| 5,051,587 A * | 9/1991 | Hara et al. | .......... | 250/584 |
| 5,072,119 A | 12/1991 | Yamaguchi | | |
| 5,422,208 A * | 6/1995 | Kojima et al. | .......... | 430/19 |
| 5,434,431 A | 7/1995 | Verbeke et al. | | |
| 5,530,261 A | 6/1996 | Yasuda | | |
| 6,339,225 B1 * | 1/2002 | Funabashi | .......... | 250/588 |
| 6,344,657 B1 * | 2/2002 | Matsumoto et al. | .......... | 250/588 |
| 7,196,345 B2 * | 3/2007 | Shimada | .......... | 250/588 |
| 7,250,622 B2 | 7/2007 | Nakajo et al. | | |
| 2002/0014606 A1 | 2/2002 | Yasuda | | |
| 2004/0089826 A1 | 5/2004 | Yonekawa | | |
| 2004/0183039 A1 | 9/2004 | Iiyama | | |
| 2005/0156126 A1 | 7/2005 | Nakajo et al. | | |
| 2005/0199837 A1 * | 9/2005 | Shimada | .......... | 250/588 |
| 2005/0211932 A1 | 9/2005 | Kuwabara | | |
| 2006/0145104 A1 | 7/2006 | Rogers et al. | | |
| 2008/0023660 A1 * | 1/2008 | Suzuki | .......... | 250/588 |

FOREIGN PATENT DOCUMENTS

| | | |
|---|---|---|
| JP | 5-119412 A | 5/1993 |
| JP | 6-175243 A | 6/1994 |

* cited by examiner

*Primary Examiner*—David P Porta
*Assistant Examiner*—David S Baker
(74) *Attorney, Agent, or Firm*—Sughrue Mion, PLLC

(57) ABSTRACT

A phototimer detects the dose of an X-ray radiation that has passed through a stimulable phosphor panel, and a stored quantity calculator calculates the quantity of radiation energy stored in the stimulable phosphor panel. An irradiation time ratio setting unit reads an irradiation time ratio from an irradiation time ratio storage unit according to the calculated quantity of radiation energy, and sets the read irradiation time ratio in an erasing unit. Based on the irradiation time ratio, the erasing unit applies erasing light including a radiation in a short wavelength range to the stimulable phosphor panel and thereafter applies erasing light comprising only a radiation in a long wavelength range to the stimulable phosphor panel, thereby erasing a residual radiation image from the stimulable phosphor panel.

17 Claims, 9 Drawing Sheets

APPARATUS FOR AND METHOD OF ERASING RESIDUAL RADIATION IMAGE

BACKGROUND OF THE INVENTION

1. Field of the Invention

The present invention relates to an apparatus for and a method of erasing a residual radiation image from a stimulable phosphor panel by applying erasing light to the stimulable phosphor panel after a radiation image has been read from the stimulable phosphor panel by applying stimulating light to the stimulable phosphor panel.

2. Description of the Related Art

There has heretofore been known a stimulable phosphor which, when exposed to radiation (X-rays, α-rays, β-rays, γ-rays, electron beams, ultraviolet radiation, or the like), stores part of the energy of the radiation, and, when subsequently exposed to stimulating rays such as visible light, emits light in proportion to the stored energy of the radiation.

A radiation image information recording and reproducing system, which has been developed in the art, temporarily records a radiation image of a subject such as a human body on a stimulable phosphor panel having a stimulable phosphor layer. Thereafter, the radiation image information recording and reproducing system applies stimulating light such as a laser beam or the like to the stimulable phosphor panel to emit light representative of the recorded radiation image, and then outputs the radiation image as a visible image on a recording medium such as a photosensitive medium or the like or a display unit such as a CRT or the like, based on an image signal that is generated by photoelectrically reading the light emitted from the stimulable phosphor panel. After the radiation image has been read from the stimulable phosphor panel, the stimulable phosphor panel is irradiated with erasing light to erase any remaining radiation image therefrom, and then used again for recording a radiation image thereon.

If erasing light exclusive of ultraviolet radiation is used to erase the remaining radiation image from the stimulable phosphor panel, then electrons trapped in a deep layer where they cannot be removed by visible erasing light tend to remain unremoved. Conversely, if erasing light including much ultraviolet radiation is used, then though those trapped electrons can be removed from the deep layer, new trapped electrons are generated by the ultraviolet-rich erasing light itself.

In order to eliminate the above drawback, there has been developed a technology for applying first erasing light including a radiation in an ultraviolet wavelength range to a stimulable phosphor panel to remove trapped electrons from a deep layer region thereof and thereafter applying second erasing light in a wavelength range other than the ultraviolet wavelength range to remove trapped electron that have newly been generated in a relatively shallow layer by the first erasing light (see Japanese Laid-Open Patent Publication No. 5-119412). The technology increases the erasing efficiency by setting the first erasing light and the second erasing light to a certain light quantity ratio.

The distribution of trapped electrons in the stimulable phosphor panel depends on the dose of a radiation that is applied thereto. For example, if the dose of an applied radiation is low, then many trapped electrons are distributed in a surface layer of the stimulable phosphor panel, and if the dose of an applied radiation is high, trapped electrons are distributed also in a deep layer of the stimulable phosphor panel. Therefore, it is necessary to take into account the dose of the radiation applied to the stimulable phosphor panel in order to reliably erase the residual radiation image remaining in the stimulable phosphor panel.

SUMMARY OF THE INVENTION

It is a general object of the present invention to provide an apparatus for and a method of efficiently and reliably erasing a residual radiation image from a stimulable phosphor panel with a required minimum level of erasing energy within a required minimum time.

A principal object of the present invention is to provide an apparatus for and a method of erasing a residual radiation image from a stimulable phosphor panel so that the stimulable phosphor panel can be reused in excellent conditions.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
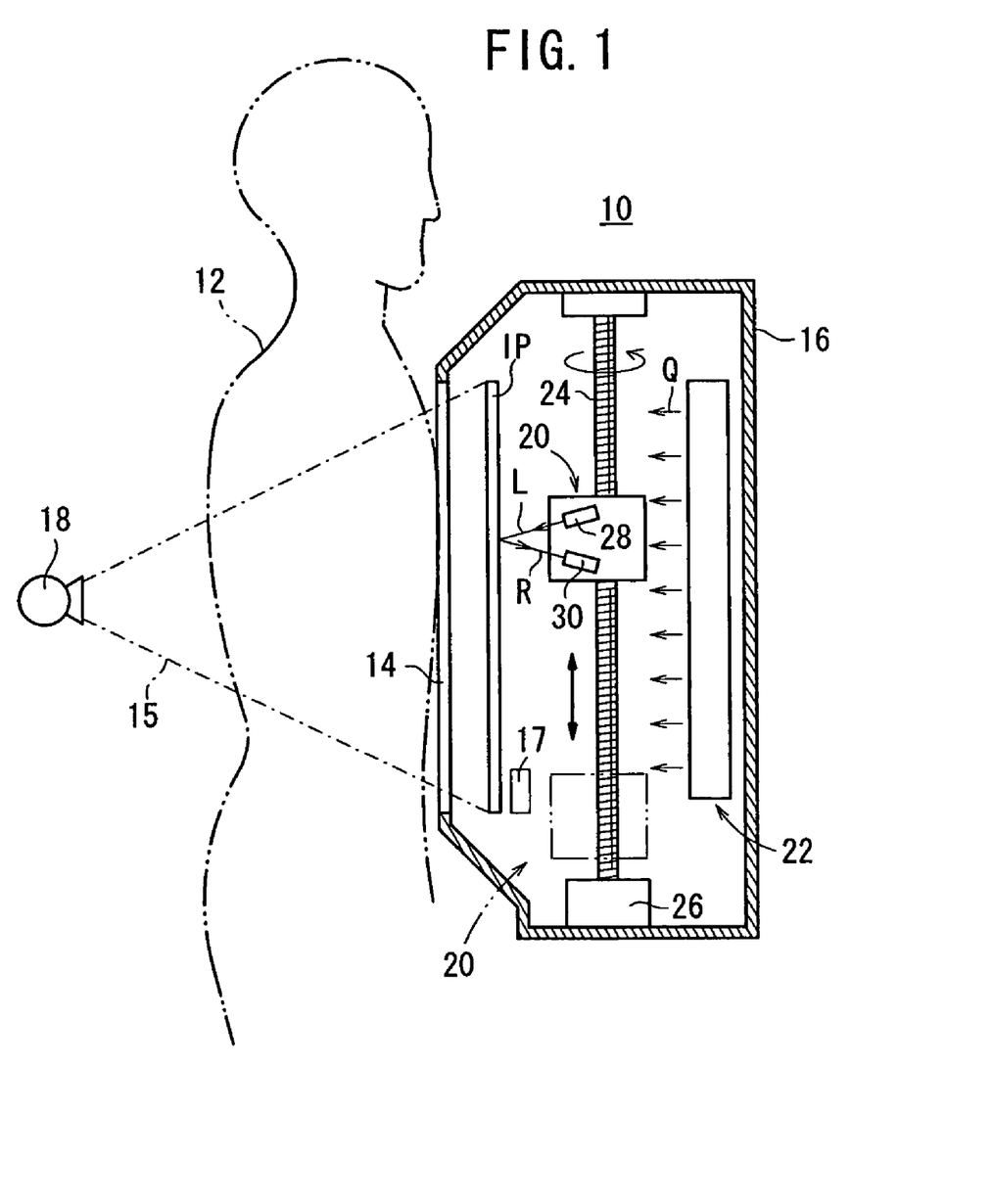
FIG. 1 is a vertical cross-sectional view of an upright imaging system incorporating therein an apparatus for and a method of erasing a residual radiation image according to the present invention.

FIG. 1 shows in vertical cross section an upright imaging system 10 incorporating therein an apparatus for and a method of erasing a residual radiation image according to the present invention.

As shown in FIG. 1, the upright imaging system 10 has, in addition to a function to record a radiation image of a subject 12 such as a human body or the like on a stimulable phosphor panel IP, a function to read a radiation image from a stimulable phosphor panel IP, and a function to erase a residual radiation image which remains in a stimulable phosphor panel IP from which a recorded radiation image has been read.

The stimulable phosphor panel IP may comprise a hard panel having a columnar stimulable phosphor layer evaporated (vapor-deposited) on a support board of a hard material such as glass or the like. The columnar stimulable phosphor layer may be formed by any of various processes including a vacuum evaporation process in which a stimulable phosphor is heated and evaporated in a vacuum container and then deposited on the support board, a sputtering process, a CVD process, and an ion plating process. The columnar stimulable phosphor layer has the stimulable phosphor formed as optically independent columns substantially perpendicular to the plane of the stimulable phosphor panel IP. The columns of the columnar stimulable phosphor are optically independent of each other, are highly sensitive to a radiation applied thereto, lower the granularity of images recorded therein, and reduce the scattering of stimulating light applied thereto for producing sharp images.

However, the stimulable phosphor panel IP is not limited to the structure wherein a columnar stimulable phosphor layer is evaporated on a support board of a hard material. The stimulable phosphor panel IP may comprise a sheet wherein a flexible support board is coated with a stimulable phosphor. In the upright imaging system 10 according to the present embodiment, the stimulable phosphor panel IP is of the type wherein a stimulable phosphor layer is evaporated on a transparent support board for recording a radiation image from one surface and reading a recorded radiation image and erasing a residual radiation image from the other surface. Dependent on the structural details of the upright imaging system 10, the stimulable phosphor panel IP may be of the type wherein a radiation image is recorded, read, and erased from one surface.

The upright imaging system 10 comprises a vertical imaging base 14 for positioning a region to be imaged of the subject 12, and a casing 16 coupled to the imaging base 14 and providing, together with the imaging base 14, a light-shielded chamber in the upright imaging system 10. An X-ray source 18 is disposed in facing relation to the imaging base 14 for applying an X-ray radiation 15 to the subject 12.

The stimulable phosphor panel IP is disposed in the casing 16 of the upright imaging system 10 substantially parallel to the imaging base 14. The casing 16 houses therein a reading unit 20 for reading a radiation image recorded in the stimulable phosphor panel IP and an erasing unit 22 for erasing a residual radiation image from the stimulable phosphor panel IP after the radiation image has been read from the stimulable phosphor panel IP. A phototimer 17 (radiation dose detector) that serves as a dose detection sensor for detecting the dose of the X-ray radiation 15 that has passed through the stimulable phosphor panel IP is disposed between the stimulable phosphor panel IP and the reading unit 20 at a position not to interfere with the reading of the radiation image by the reading unit 20.

The reading unit 20 is threaded over a ball screw 24 extending vertically in the casing 16. When the ball screw 24 is rotated about its own axis by a motor 26 coupled to the lower end of the ball screw 24 in a direction indicated by an arrow, the reading unit 20 is vertically moved on and along the ball screw 24. The reading unit 20 comprises a stimulating light source 28 for applying stimulating light L in a wavelength range from 600 to 750 nm, for example, to the stimulable phosphor panel IP on which a radiation image has been recorded, and a photoelectric transducer 30 for detecting stimulated light R representing the radiation image which is emitted from the stimulable phosphor panel IP when it is irradiated with the stimulating light L, and converting the stimulated light R into an electric signal.

The stimulating light source 28 may comprise a linear array of light-emitting diodes extending along the main scanning direction, i.e., a direction normal to the sheet of FIG. 1, of the stimulable phosphor panel IP. The photoelectric transducer 30 may comprise a CCD line sensor for detecting the stimulated light R emitted from the stimulable phosphor panel IP when the stimulating light L from the stimulating light source 28 is applied to the stimulable phosphor panel IP while scanning the stimulable phosphor panel IP in the main scanning direction. At this time, the reading unit 20 may be moved in the auxiliary scanning direction indicated by the arrow along the ball screw 24, i.e., the stimulable phosphor panel IP, so that the radiation image recorded in the stimulable phosphor panel IP can be read two-dimensionally.

Figure 2:
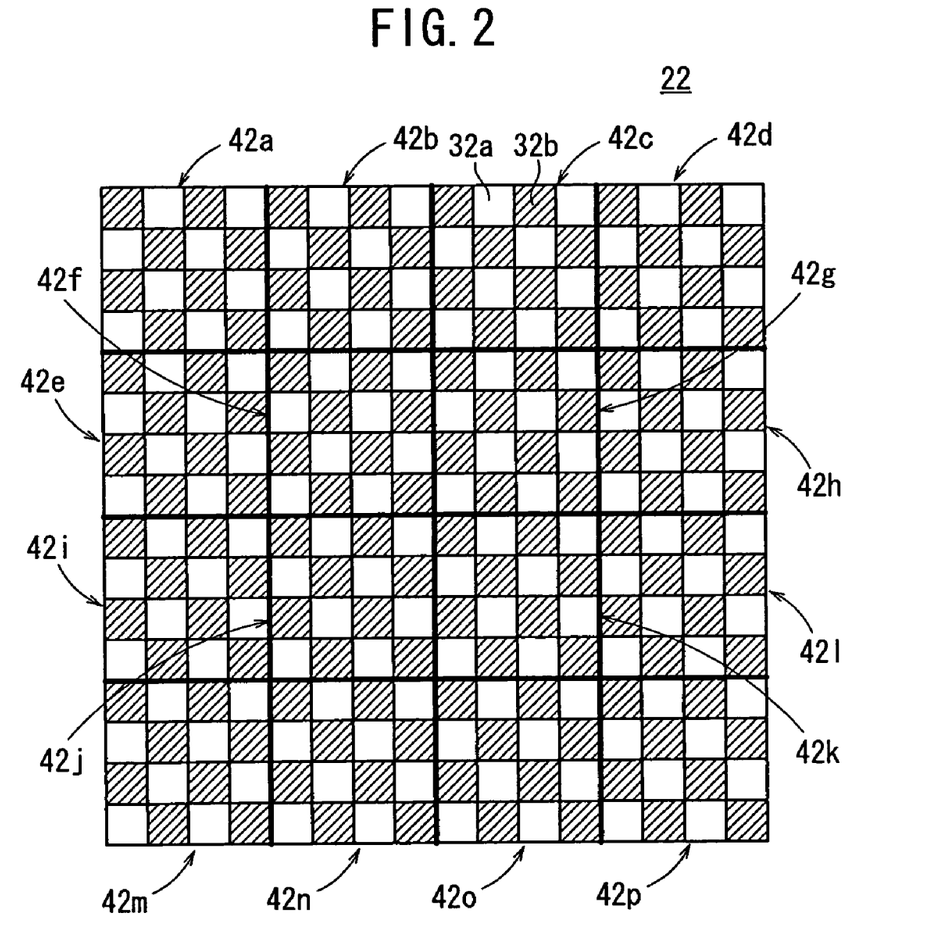
FIG. 2 is a view of erasing light sources of an erasing unit in the upright imaging system shown in FIG. 1.

The erasing unit 22 is disposed in confronting relation to the stimulable phosphor panel IP across the reading unit 20. As shown in FIG. 2, the erasing unit 22 comprises a number of erasing light sources 32a, 32b, each for emitting erasing light Q, alternately arranged in a two-dimensional matrix.

Each of the erasing light sources 32a (first erasing elements) emits first erasing light Q1 including a radiation in a wavelength range shorter than 500 nm, and each of the erasing light sources 32b (second erasing elements) emits second erasing light Q2 comprising only a radiation in a wavelength range equal to or longer than 500 nm. These erasing light sources 32a, 32b may comprise light-emitting elements such as light-emitting diodes or the like. Alternatively, each of the erasing light sources 32a, 32b may emit erasing light Q including a radiation in a short wavelength range and a radiation in a long wavelength range, with a filter being disposed in front of each of the erasing light sources 32b for filtering out the radiation in the short wavelength range.

Figure 3:
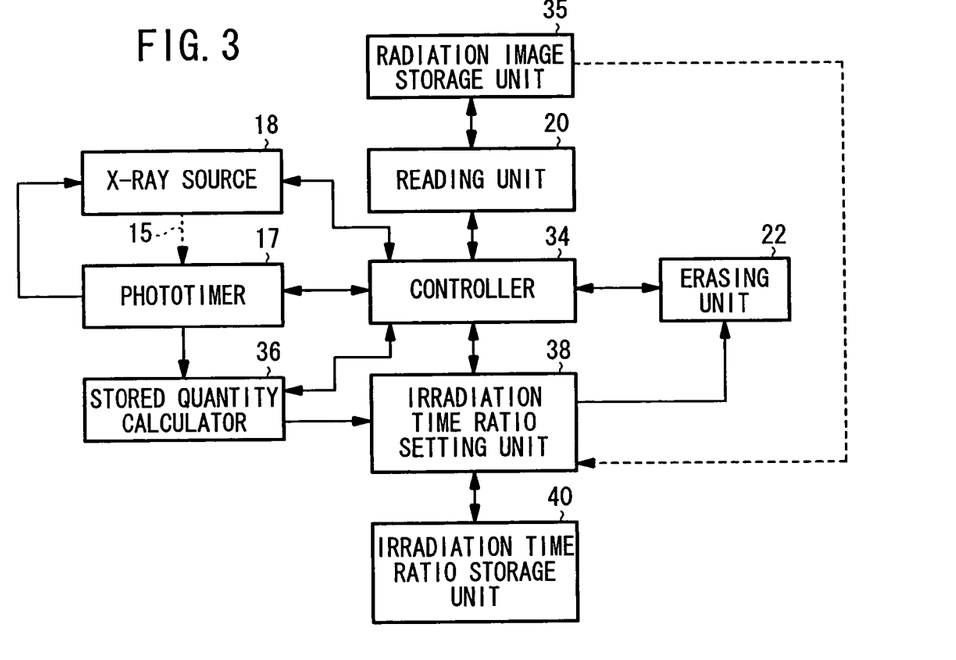
FIG. 3 is a block diagram of a control circuit in the upright imaging system shown in FIG. 1.

FIG. 3 shows in block form a control circuit of the upright imaging system 10.

As shown in FIG. 3, the upright imaging system 10 is controlled by a controller 34. Specifically, the controller 34 controls the X-ray source 18 according to the imaging conditions, and also controls the reading unit 20 and the erasing unit 22. A radiation image that has been read from the stimulable phosphor panel IP by the reading unit 20 is stored in a radiation image storage unit 35.

The phototimer 17 detects the dose of the X-ray radiation 15 that has passed through the subject 12 and the stimulable phosphor panel IP. If the detected dose exceeds a predetermined upper limit dose set depending on the subject region to be imaged, the imaging conditions, etc., then the phototimer 17 forcibly stops supplying a high voltage to the X-ray source 18, thereby preventing in advance the subject 12 from being excessively exposed to the X-ray radiation 15. The dose of the X-ray radiation 15 which is detected by the phototimer 17 is supplied to a stored quantity calculator 36, which calculates the quantity of radiation energy stored in the stimulable phosphor panel IP. The phototimer 17 and the stored quantity calculator 36 jointly make up a stored quantity detecting means.

The quantity of radiation energy calculated by the stored quantity calculator 36 is supplied to an irradiation time ratio setting unit 38 (ratio setting means). The irradiation time ratio setting unit 38 reads an optimum irradiation time ratio for the first erasing light Q1 and the second erasing light Q2 with respect to the calculated quantity of stored radiation energy, from an irradiation time ratio storage unit 40, and supplies the read optimum irradiation time ratio to the erasing unit 22.

The irradiation time ratio storage unit 40 stores beforehand optimum irradiation time ratios for the first erasing light Q1 and the second erasing light Q2 with respect to the quantities of radiation energy that may be stored in the stimulable phosphor panel IP.

Figure 4:
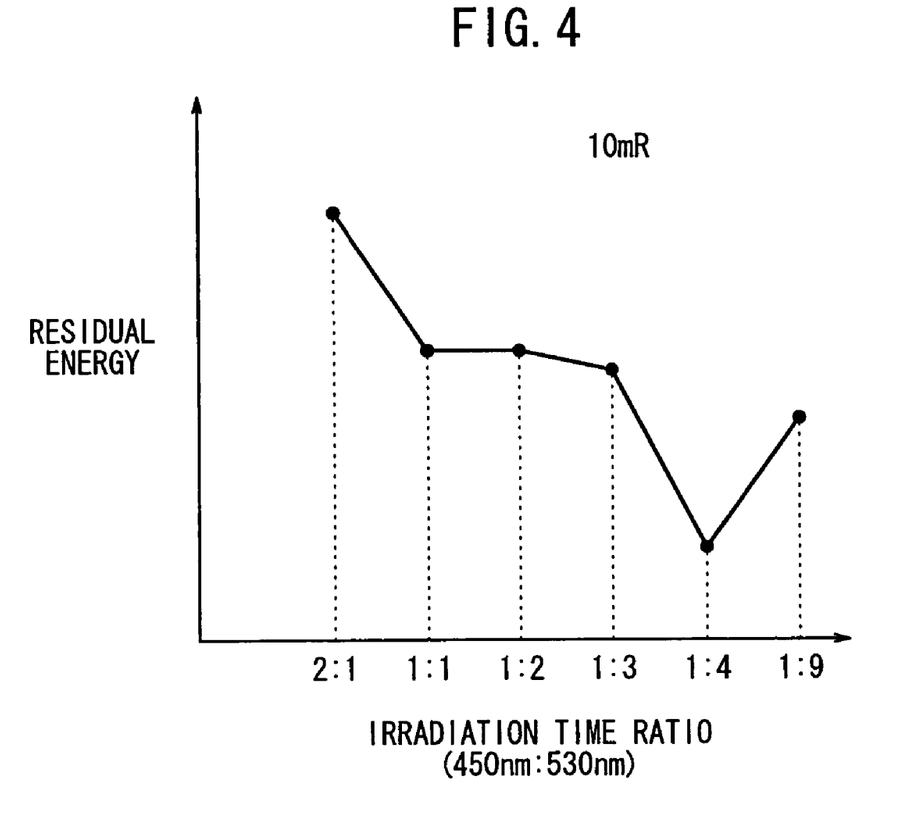
FIG. 4 is a diagram showing the relationship between irradiation time ratios and amounts of remaining energy at the time the dose of radiation energy is 10 mR.
Figure 5:
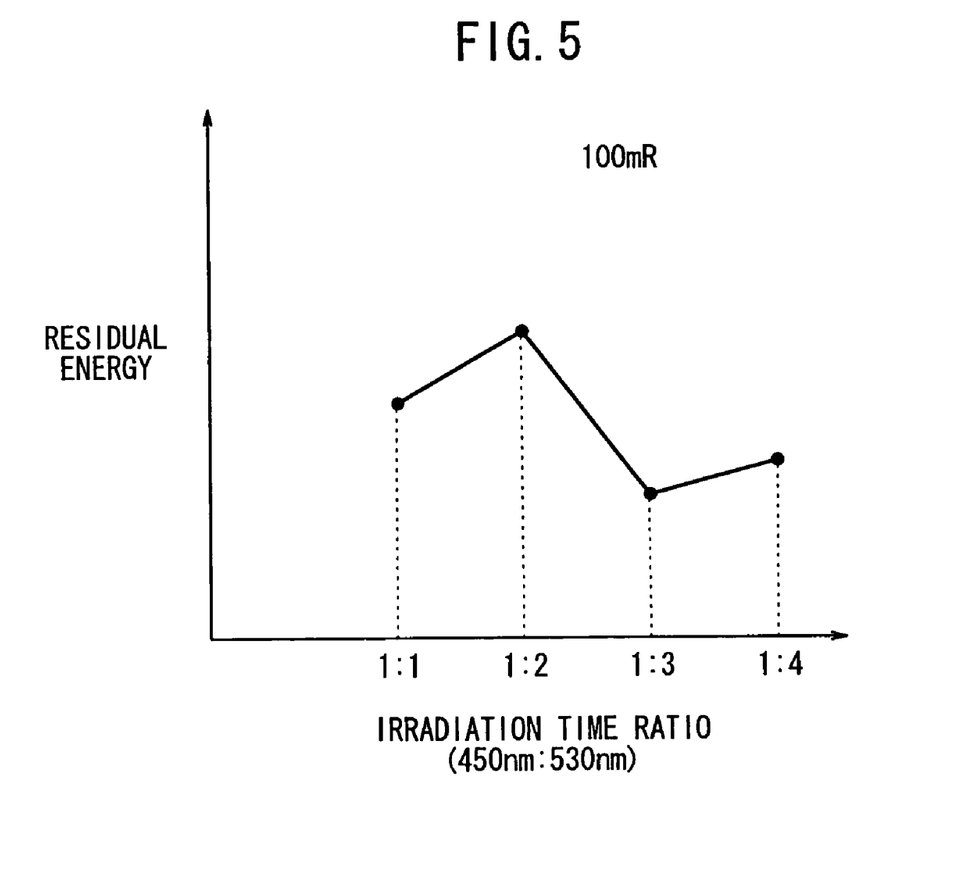
FIG. 5 is a diagram showing the relationship between irradiation time ratios and amounts of remaining energy at the time the dose of radiation energy is 100 mR.
Figure 6:
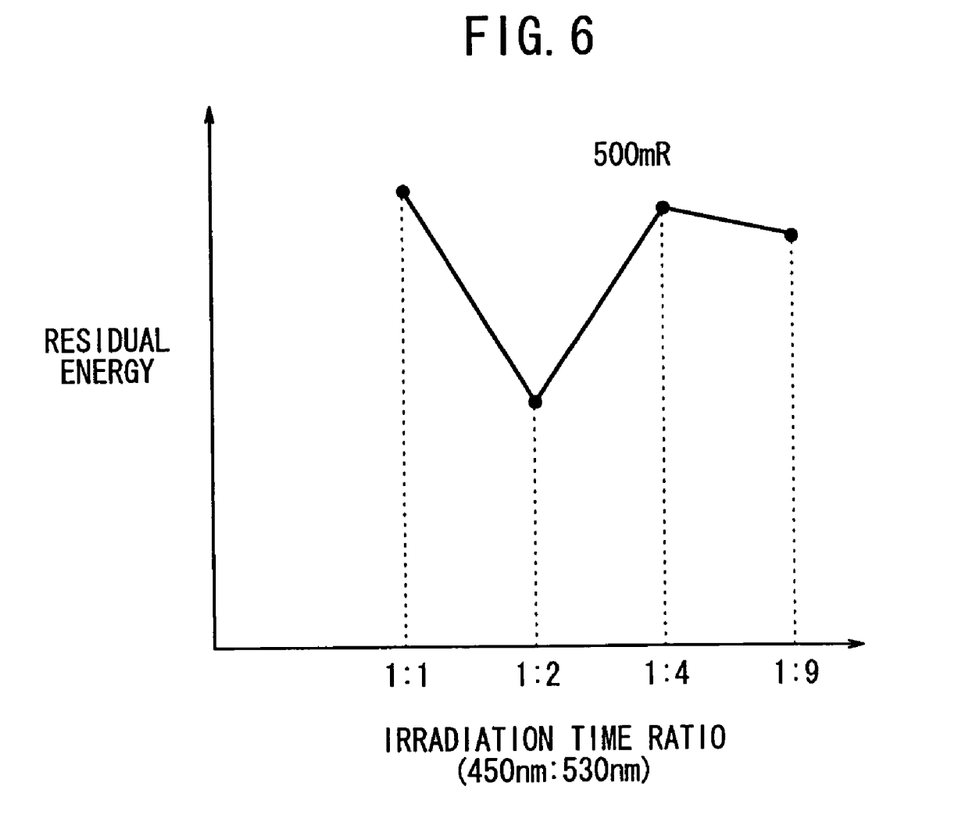
FIG. 6 is a diagram showing the relationship between irradiation time ratios and amounts of remaining energy at the time the dose of radiation energy is 500 mR.

The applicant of the present application combined doses of the X-ray radiation 15 applied to the stimulable phosphor panel IP and irradiation time ratios of the first erasing light Q1 having a wavelength of 450 nm and the second erasing light Q2 having a wavelength of 530 nm in various combinations, applied the first erasing light Q1 and the second erasing light Q2 at a given irradiation energy level to the stimulable phosphor panel IP for 90 seconds, and thereafter measured amounts of energy remaining in the stimulable phosphor panel IP. The measured values are shown in FIGS. 4 through 6. FIG. 4 illustrates measured results obtained when the dose of the X-ray radiation 15 was 10 mR ($\approx 2.58 \times 10^{-6}$ C/kg), FIG. 5 measured results obtained when the dose of the X-ray radiation 15 was 100 mR ($\approx 2.58 \times 10^{-5}$ C/kg), and FIG. 6 measured results obtained when the dose of the X-ray radiation 15 was 500 mR ($\approx 1.29 \times 10^{-4}$ C/kg).

It can be seen from the illustrated measured results that when the dose of the X-ray radiation 15 is low (see FIG. 4), if the irradiation time ratio of the first erasing light Q1 to the second erasing light Q2 is smaller, the amount of energy remaining in the stimulable phosphor panel IP is reduced, indicating that the remaining radiation image can efficiently be erased. It can also be understood that when the dose of the X-ray radiation 15 is high (see FIG. 6), if the irradiation time ratio of the first erasing light Q1 to the second erasing light Q2 is greater than the case when the dose of the X-ray radiation 15 is low, the amount of energy remaining in the stimulable phosphor panel IP is reduced, indicating that the remaining radiation image can efficiently be erased.

The reasons for the above measured results are that when the dose of the X-ray radiation 15 is low, trapped electrons distributed in a deep layer of the stimulable phosphor panel IP are reduced, and much of the first erasing light Q1 including the high-energy radiation in the short wavelength range is not required, but primarily the second erasing light Q2 including the radiation in the long wavelength range is applied to the stimulable phosphor panel IP, thereby sufficiently removing the trapped electrons. On the other hand, when the dose of the X-ray radiation 15 is high, trapped electrons distributed in a deep layer of the stimulable phosphor panel IP are increased, and the first erasing light Q1 including the high-energy radiation in the short wavelength range is applied to the stimulable phosphor panel IP for a relatively long period of time to remove the trapped electrons in the deep layer. Thereafter, the second erasing light Q2 including the radiation in the long wavelength range is applied to the stimulable phosphor panel IP, thereby sufficiently removing the trapped electrons.

Based on the above measured results, the irradiation time ratio storage unit 40 stores irradiation time ratios for the first erasing light Q1 and the second erasing light Q2, which are capable of minimizing the residual radiation energy, with respect to the quantities of radiation energy that are stored in the stimulable phosphor panel IP depending on the dose of the X-ray radiation 15 applied to the stimulable phosphor panel IP.

The upright imaging system 10 according to the present embodiment is basically constructed as described above. Operation and advantages of the upright imaging system 10 will be described below.

It is assumed that the stimulable phosphor panel IP from which any residual radiation image has completely been erased is set in the upright imaging system 10. After the subject 12 is positioned in a given area on the imaging base 14, the X-ray source 18 is controlled according to the subject region to be imaged, the imaging conditions, etc. to apply the X-ray radiation 15 to the subject 12.

Part of the X-ray radiation 15 applied to the subject 12 passes through the subject 12 and is applied to the stimulable phosphor panel IP, recording a radiation image of the subject 12 in the stimulable phosphor panel IP. The X-ray radiation 15 that has passed through the stimulable phosphor panel IP is detected by the phototimer 17. When the phototimer 17 determines that the detected dose of the X-ray radiation 15 exceeds a prescribed value that has been set according to the imaging conditions, etc., the phototimer 17 outputs a turn-off signal to the X-ray source 18 to prevent the X-ray source 18 from outputting the X-ray radiation 15.

The dose of the X-ray radiation 15 which is detected by the phototimer 17 is supplied to the stored quantity calculator 36, which calculates the quantity of radiation energy stored in the stimulable phosphor panel IP from the supplied dose. The calculated quantity of stored radiation energy is supplied to the irradiation time ratio setting unit 38. The irradiation time ratio setting unit 38 reads an irradiation time ratio for the first erasing light Q1 and the second erasing light Q2 with respect to the calculated quantity of radiation energy, from the irradiation time ratio storage unit 40, and supplies the read irradiation time ratio to the erasing unit 22.

After the radiation image is recorded in the stimulable phosphor panel IP, the reading unit 20 is energized to start reading the radiation image from the stimulable phosphor panel IP. Specifically, the motor 26 is energized to rotate the ball screw 24 about its own axis, moving the reading unit 20 in the auxiliary scanning direction indicated by the arrow along the stimulable phosphor panel IP. At this time, the stimulating light L emitted from the stimulating light source 28 is applied as a line of light in the main scanning direction to the stimulable phosphor panel IP. Upon exposure to the stimulating light L, the stimulable phosphor panel IP emits stimulated light R which depends on the recorded radiation image. The stimulated light R emitted from the stimulable phosphor panel IP is converted by the photoelectric transducer 30 into an electric signal, which is stored as representing the radiation image in the radiation image storage unit 35. In this manner, the radiation image recorded in the stimulable phosphor panel IP is two-dimensionally read from the stimulable phosphor panel IP.

After the reading unit 20 has read the radiation image recorded in the stimulable phosphor panel IP, the erasing unit 22 is energized to start erasing a residual radiation image in the stimulable phosphor panel IP. The erasing unit 22 has an irradiation time ratio for the first erasing light Q1 and the second erasing light Q2, set therein by the irradiation time ratio setting unit 38 according to the quantity of radiation energy stored in the stimulable phosphor panel IP.

First, the erasing light sources 32a shown in FIG. 2 are energized to apply only the first erasing light Q1 of the given irradiation energy including the radiation in the wavelength range shorter than 500 nm for the irradiation time according to the set irradiation time ratio, to the stimulable phosphor panel IP. Trapped electrons remaining in the deep layer of the stimulable phosphor panel IP due to the applied X-ray radiation 15 are now reliably removed by the required minimum first erasing light Q1.

Then, the erasing light sources 32b shown in FIG. 2 are energized to apply only the second erasing light Q2 of the given irradiation energy including the radiation in the wavelength range equal to or longer than 500 nm for the irradiation time according to the set irradiation time ratio, to the stimulable phosphor panel IP. Trapped electrons remaining in the relatively shallow layer of the stimulable phosphor panel IP are now reliably removed by the required minimum second erasing light Q2.

As described above, the residual radiation image remaining in the stimulable phosphor panel IP can reliably be removed therefrom. As no significant radiation image remains in the stimulable phosphor panel IP after it has been processed by the erasing unit 22, a new radiation image can be recorded highly accurately in the stimulable phosphor panel IP without being adversely affected by any residual radiation image.

In the above embodiment, the quantity of radiation energy stored in the stimulable phosphor panel IP is calculated from the dose of the X-ray radiation 15 which is detected by the phototimer 17. However, the quantity of radiation energy stored in the stimulable phosphor panel IP may be calculated based on the radiation image read by the reading unit 20, for example. According to such a modification, a maximum quantity of stored radiation energy may be calculated from a maximum energy level of the radiation image read by the reading unit 20, and an irradiation time ratio may be set for the first erasing light Q1 and the second erasing light Q2 based on the calculated maximum quantity of stored radiation energy.

As shown in FIG. 2, the erasing light sources 32a, 32b of the erasing unit 22 may be divided into a plurality of blocks 42a through 42p. The amount of stored radiation energy may be calculated with respect to each of divided areas of the stimulable phosphor panel IP which correspond respectively to the blocks 42a through 42p, and each of erasure time ratios for the erasing light sources 32a, 32b in the blocks 42a through 42p may be set from the calculated amount of stored radiation energy. The erasing light sources 32a, 32b in each of the blocks 42a through 42p may then be controlled according to the erasure time ratio for erasing any residual radiation image from the stimulable phosphor panel IP. With this arrangement, the residual radiation image remaining in the stimulable phosphor panel IP can be removed thoroughly from the stimulable phosphor panel IP with a required minimum amount of erasing energy. The amount of stored radiation energy in each of the divided areas of the stimulable phosphor panel IP can be calculated from the dose of the radiation energy detected by each of phototimers 17 arranged in a two-dimensional matrix along the stimulable phosphor panel IP or from the radiation image read from each of the divided areas of the stimulable phosphor panel IP by the reading unit 20.

Figure 7:
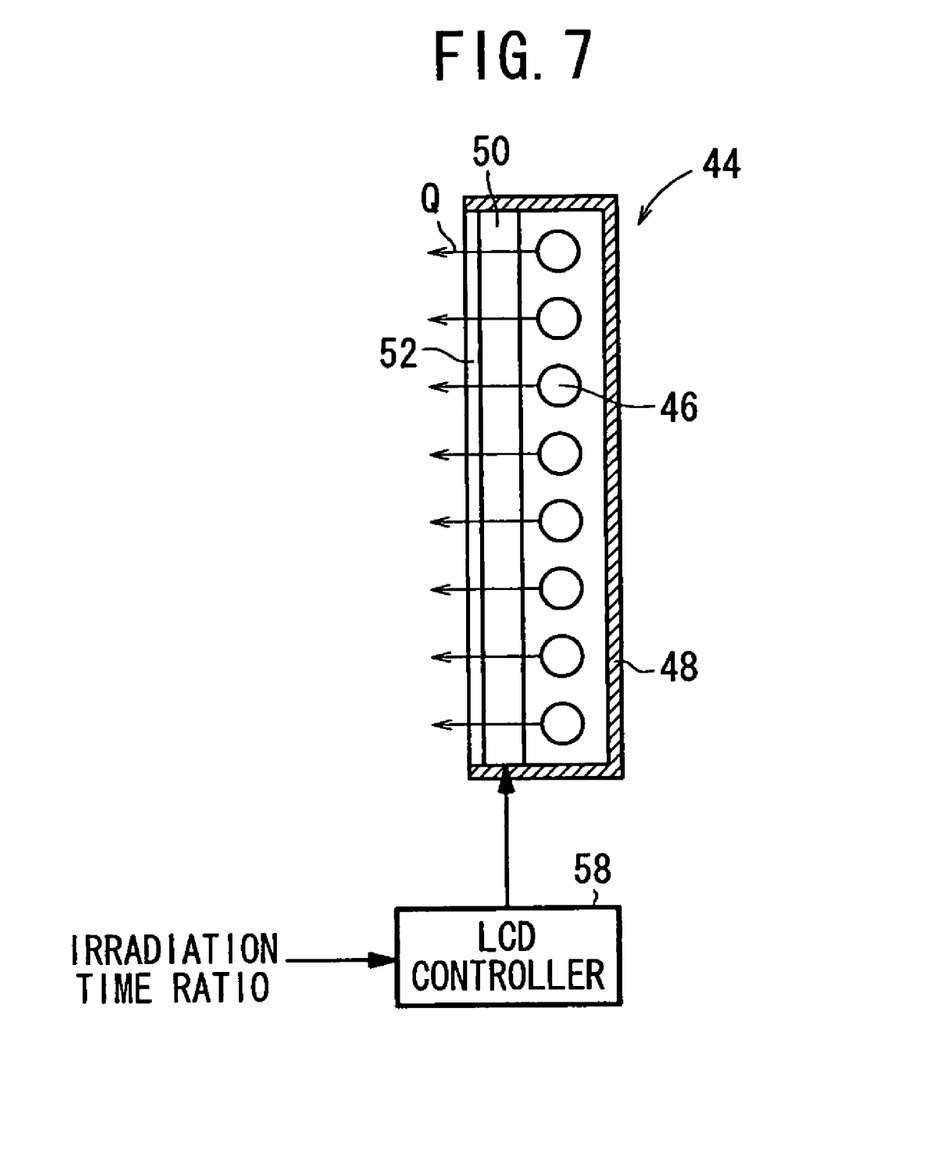
FIG. 7 is a vertical cross-sectional view of an erasing unit according to another embodiment of the present invention.

FIG. 7 shows in vertical cross section an erasing unit 44 according to another embodiment of the present invention. As shown in FIG. 7, the erasing unit 44 comprises a plurality of erasing light sources 46 housed in a casing 48 for emitting erasing light Q through an opening of the casing 48, and an LCD (Liquid Crystal Display) panel 50 and a filter 52 that are mounted in the opening of the casing 48. Each of the erasing light sources 46 comprises a xenon tube, a cold-cathode tube, or the like which is capable of emitting erasing light Q in a full wavelength range covering short to long wavelengths for erasing residual radiation energy. The LCD panel 50 and the filter 52 jointly make up a filtering mechanism.

Figure 8:
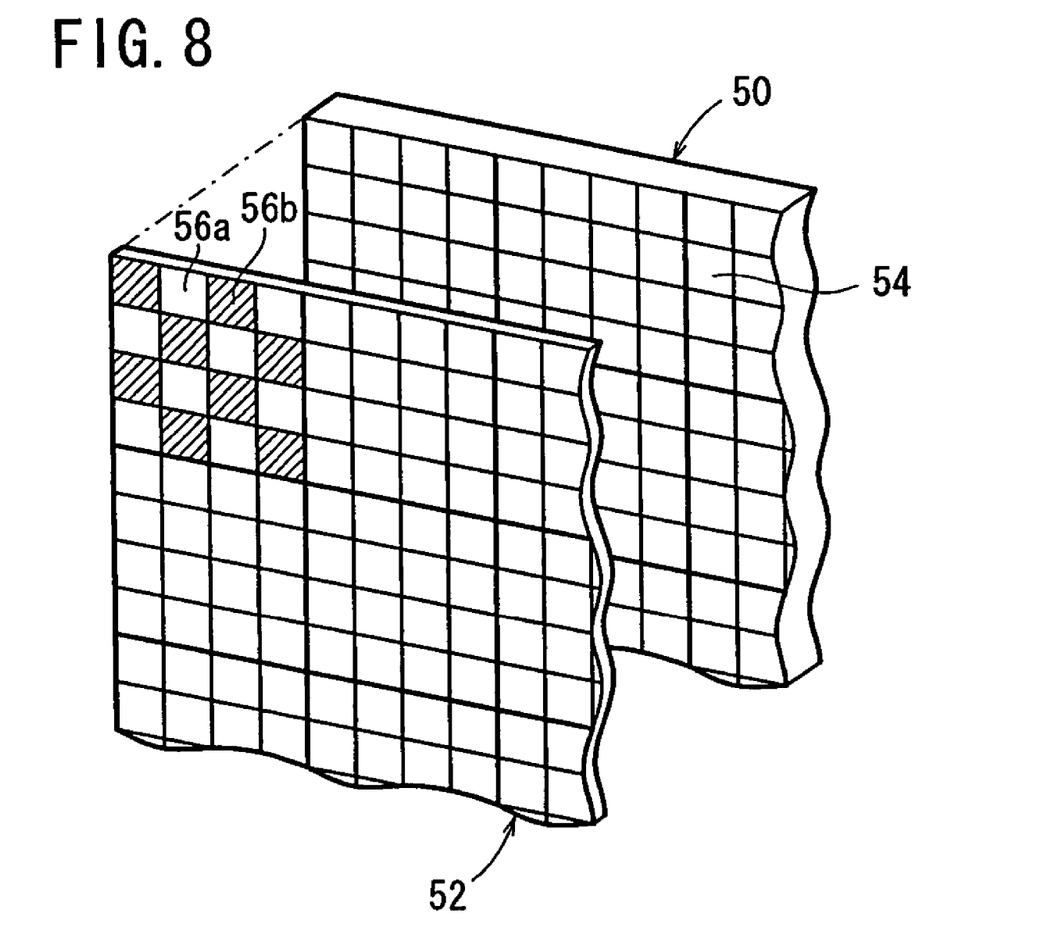
FIG. 8 is a fragmentary perspective view of a filtering mechanism of the erasing unit shown in FIG. 7.

As shown in FIG. 8, the LCD panel comprises a matrix of LCD devices 54 (liquid crystal shutters). The filter 52 comprises a number of filter elements 56a, 56b alternately arranged in a two-dimensional matrix corresponding to the respective LCD devices 54. The filter elements 56a serve to pass the erasing light Q (first erasing light Q1) in the full wavelength range, and the filter elements 56b (short-wavelength radiation cut-off filter) serve to pass the erasing light Q (second erasing light Q2) in a wavelength range exclusive of the short wavelength range. The filter elements 56a may be dispensed with.

The erasing unit 44 operates as follows: An LCD controller 58 (see FIG. 7) is controlled according to the irradiation time ratio supplied from the irradiation time ratio setting unit 38. Specifically, the LCD controller 58 is controlled to render those LCD devices 54 corresponding to the filter elements 56a transmissive, applying the first erasing light Q1 including the radiation in the short wavelength range to the stimulable phosphor panel IP for a given time based on the irradiation time ratio. Thereafter, the LCD controller 58 is controlled to render those LCD devices 54 corresponding to the filter elements 56b transmissive, applying the second erasing light Q2 exclusive of the radiation in the short wavelength range to the stimulable phosphor panel IP for a given time based on the irradiation time ratio. As a result, the residual radiation image remaining in the stimulable phosphor panel IP can reliably be removed from the stimulable phosphor panel IP. As with the erasing unit 22 shown in FIG. 2, the LCD devices 54 may be divided into a plurality of blocks, and an irradiation time ratio may be set for each of the blocks for controlling irradiation times in the respective blocks. According to such a modification, the residual radiation image remaining in the stimulable phosphor panel IP can also be removed thoroughly from the stimulable phosphor panel IP with a required minimum amount of erasing energy.

Figure 9:
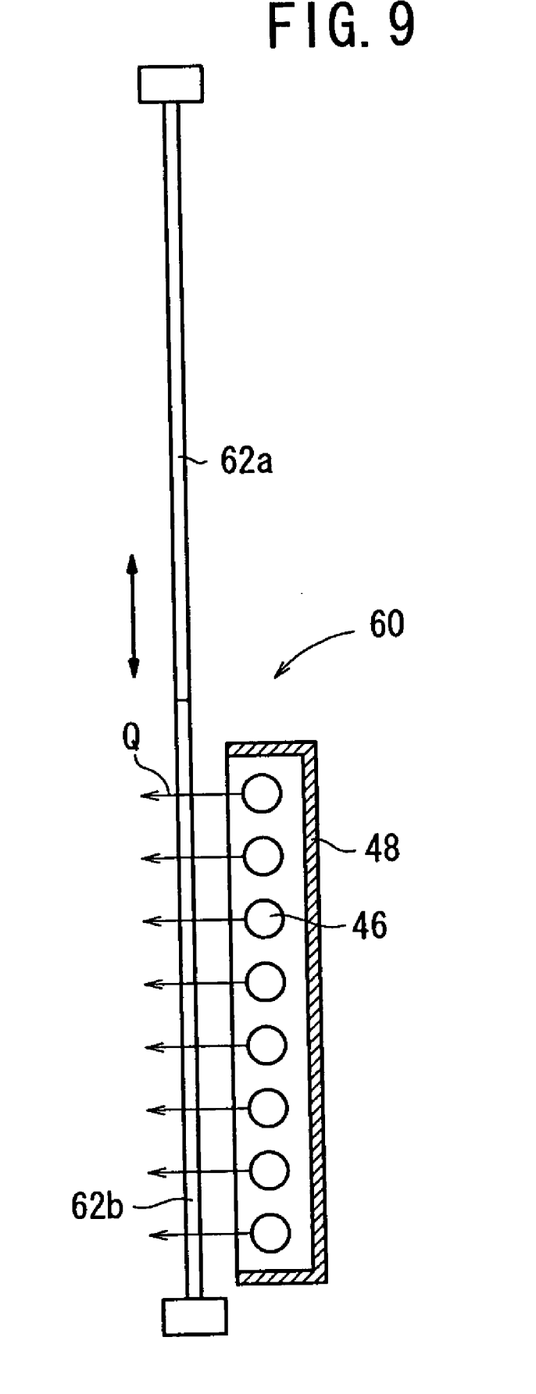
FIG. 9 is a vertical cross-sectional view of an erasing unit according to still another embodiment of the present invention.

FIG. 9 shows in vertical cross section an erasing unit 60 according to still another embodiment of the present invention. As shown in FIG. 9, the erasing unit 60 comprises a plurality of erasing light sources 46 housed in a casing 48 for emitting erasing light Q through an opening of the casing 48, and two filters 62a, 62b that are selectively positionable in front of the opening of the casing 48. Each of the erasing light sources 46 is capable of emitting erasing light Q in a full wavelength range for erasing residual radiation energy as with the erasing unit 44. The filter 62a serves to pass the erasing light Q (first erasing light Q1) in the full wavelength range, and the filter 62b (short-wavelength radiation cut-off filter) serves to pass the erasing light Q (second erasing light Q2) in a wavelength range exclusive of the short wavelength range.

The erasing unit 60 thus constructed is able to reliably erase any residual radiation image from the stimulable phosphor panel IP by moving the filters 62a, 62b selectively in the directions indicated by the arrows into the position in front of the opening of the casing 48 according to the irradiation time ratio set by the irradiation time ratio setting unit 38.

Although certain preferred embodiments of the present invention have been shown and described in detail, it should be understood that various changes and modifications may be made therein without departing from the scope of the appended claims.

What is claimed is:

1. An apparatus for erasing a residual radiation image from a stimulable phosphor panel by applying erasing light to the stimulable phosphor panel after a radiation image has been read from the stimulable phosphor panel by applying stimulating light to the stimulable phosphor panel, comprising:

an erasing unit for applying first erasing light including a radiation in a first wavelength range to said stimulable phosphor panel, and thereafter applying second erasing light comprising only a radiation in a second wavelength range to said stimulable phosphor panel;

stored quantity detecting means for detecting a quantity of radiation energy stored in said stimulable phosphor panel; and ratio setting means for setting an irradiation time ratio for said first erasing light and said second erasing light to be applied to said stimulable phosphor panel, according to said quantity of radiation energy stored in said stimulable phosphor panel;

wherein said erasing unit is controlled according to the irradiation time ratio set by said ratio setting means, wherein, a first wavelength range comprises wavelengths that are shorter than those of the second wavelength range.

2. An apparatus according to claim 1, wherein said erasing unit comprises:
   a first erasing light source for emitting said first erasing light; and
   a second erasing light source for emitting said second erasing light;
   wherein said first erasing light source and said second erasing light source have respective energization times controlled according to said irradiation time ratio set by said ratio setting means.

3. An apparatus according to claim 2, wherein said first erasing light source and said second erasing light source comprise a plurality of light-emitting elements arranged in a matrix in confronting relation to said stimulable phosphor panel, and said light-emitting elements of said first erasing light source and said light-emitting elements of said second erasing light source have respective energization times controlled according to said irradiation time ratio set by said ratio setting means.

4. An apparatus according to claim 3, wherein said stored quantity detecting means detects a quantity of radiation energy stored in said stimulable phosphor panel with respect to each of divided areas thereof;
   wherein said ratio setting means sets said irradiation time ratio with respect to each of said divided areas from said quantity of radiation energy with respect to each of said divided areas; and
   wherein the energization times of said light-emitting elements, which correspond to said divided areas of said stimulable phosphor panel, are controlled according to said irradiation time ratio set by said ratio setting means with respect to each of said divided areas.

5. An apparatus according to claim 1, wherein said erasing unit comprises:
   an erasing light source for emitting said first erasing light and said second erasing light; and
   a filtering mechanism disposed between said erasing light source and said stimulable phosphor panel, for selectively passing therethrough said first erasing light and said second erasing light according to said irradiation time ratio set by said ratio setting means.

6. An apparatus according to claim 5, wherein said filtering mechanism comprises:
   a plurality of liquid crystal shutters disposed between said erasing light source and said stimulable phosphor panel, for selectively transmitting and blocking said first erasing light and said second erasing light; and
   a short-wavelength radiation cut-off filter disposed in combination with selected one or more of said liquid crystal shutters, for blocking at least the radiation in the first wavelength range of said first erasing light;
   wherein said first erasing light is applied to said stimulable phosphor panel through those liquid crystal shutters that are rendered transmissive which are not disposed in combination with said short-wavelength radiation cut-off filter, and thereafter said second erasing light is applied to said stimulable phosphor panel through those liquid crystal shutters that are rendered transmissive which are disposed in combination with said short-wavelength radiation cut-off filter.

7. An apparatus according to claim 6, wherein said stored quantity detecting means detects a quantity of radiation energy stored in said stimulable phosphor panel with respect to each of divided areas thereof;
   wherein said ratio setting means sets said irradiation time ratio with respect to each of said divided areas from said quantity of radiation energy with respect to each of said divided areas; and
   wherein said liquid crystal shutters, which correspond respectively to said divided areas, control irradiation times of said first erasing light and said second erasing light according to said irradiation time ratio set by said ratio setting means with respect to each of said divided areas.

8. An apparatus according to claim 5, wherein said filtering mechanism comprises:
   a short-wavelength radiation cut-off filter insertable between said erasing light source and said stimulable phosphor panel, for blocking the radiation in said first wavelength range;
   wherein said short-wavelength radiation cut-off filter is selectively inserted between said erasing light source and said stimulable phosphor panel according to said irradiation time ratio set by said ratio setting means.

9. An apparatus according to claim 1, wherein said stored quantity detecting means has a radiation dose detector for detecting a dose of radiation applied to said stimulable phosphor panel, and said stored quantity detecting means calculates the quantity of radiation energy stored in said stimulable phosphor panel from the detected dose of radiation.

10. An apparatus according to claim 1, wherein said stored quantity detecting means calculates the quantity of radiation energy stored in said stimulable phosphor panel from said radiation image read from said stimulable phosphor panel.

11. An apparatus according to claim 1, wherein said ratio setting means has a ratio storage unit for storing a relationship between said quantity of radiation energy stored in said stimulable phosphor panel and said irradiation time ratio, and said ratio setting means reads said irradiation time ratio corresponding to said quantity of radiation energy from said ratio storage unit and sets the read irradiation time ratio.

12. An apparatus according to claim 1, wherein said irradiation time ratio is established such that the proportion of said first erasing light to said second erasing light increases as said quantity of radiation energy increases.

13. An apparatus according to claim 1, wherein said first erasing light includes a radiation in said first wavelength range shorter than 500 nm, and said second erasing light comprises only a radiation in said second wavelength range equal to or longer than 500 nm.

14. An apparatus according to claim 1, wherein said first erasing light and said second erasing light are projected in a flash manner, wherein movement of the panel or the lights is not necessary.

15. A method of erasing a residual radiation image from a stimulable phosphor panel by applying erasing light to the stimulable phosphor panel after a radiation image has been read from the stimulable phosphor panel by applying stimulating light to the stimulable phosphor panel, comprising the steps of:
   detecting a quantity of radiation energy stored in said stimulable phosphor panel;
   setting an irradiation time ratio for first erasing light and second erasing light to be applied to said stimulable phosphor panel, according to said quantity of radiation energy stored in said stimulable phosphor panel;
   applying said first erasing light which includes a radiation in a first wavelength range to said stimulable phosphor panel for an irradiation time depending on said irradiation time ratio; and thereafter, applying said second erasing light which comprises only a radiation in a second wavelength range to said stimulable phosphor panel for an irradiation time depending on said irradiation time ratio, wherein, having a first wavelength range comprises wavelengths that are shorter than those of the second wavelength range.

16. A method according to claim 15, wherein said first erasing light includes a radiation in said first wavelength range shorter than 500 nm, and said second erasing light comprises only a radiation in said second wavelength range equal to or longer than 500 nm.

17. A method according to claim 15, wherein said first erasing light and said second erasing light are projected in a flash manner, wherein movement of the panel or the lights is not necessary.

* * * * *